United States Patent [19]

Lantzsch et al.

[11] Patent Number: 4,622,333

[45] Date of Patent: Nov. 11, 1986

[54] FUNGICIDAL HYDROXYALKYNYL-AZOLYL DERIVATIVES

[75] Inventors: Reinhard Lantzsch, Leverkusen; Klaus Ditgens, Wuppertal; Karl H. Büchel, Burscheid; Paul Reinecke, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 547,806

[22] Filed: Nov. 1, 1983

[30] Foreign Application Priority Data

Nov. 15, 1982 [DE] Fed. Rep. of Germany ....... 3242222

[51] Int. Cl.[4] .................. A01N 43/50; A01N 43/653; C07D 405/6
[52] U.S. Cl. ..................... 514/383; 514/184; 514/189; 514/397; 548/101; 548/262; 548/336
[58] Field of Search .............. 548/101, 262, 341, 336; 424/245, 269, 273 R

[56] References Cited

U.S. PATENT DOCUMENTS

| 4,321,272 | 3/1982 | Walker | 548/336 |
|---|---|---|---|
| 4,496,388 | 1/1985 | Clough | 71/76 |
| 4,507,140 | 3/1985 | Sugaranam | 514/383 |

FOREIGN PATENT DOCUMENTS

| 0043419 | 1/1982 | European Pat. Off. | 548/262 |
|---|---|---|---|
| 0052424 | 5/1982 | European Pat. Off. | 548/262 |
| 0057864 | 8/1982 | European Pat. Off. | 548/262 |
| 0078594 | 5/1983 | European Pat. Off. | 548/262 |
| 2951163 | 7/1981 | Fed. Rep. of Germany | 424/269 |
| 3025308 | 1/1982 | Fed. Rep. of Germany | 548/262 |
| 3141819 | 6/1982 | Fed. Rep. of Germany | 548/341 |
| 3048267 | 7/1982 | Fed. Rep. of Germany | 548/262 |
| 3106076 | 9/1982 | Fed. Rep. of Germany | 548/262 |
| 3124580 | 1/1983 | Fed. Rep. of Germany | 548/262 |

*Primary Examiner*—Alton D. Rollins
*Attorney, Agent, or Firm*—Sprung Horn Kramer & Woods

[57] ABSTRACT

Hydroxyalkynyl-azolyl derivatives of the formula

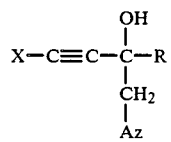

in which
Az is 1,2,4-triazolyl or imidazolyl,
X is optionally substituted phenyl or alkyl,
R is

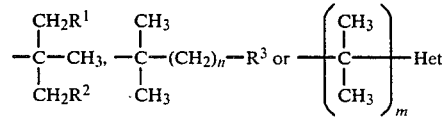

$R^1$ is hydrogen or halogen,
$R^2$ is halogen,
$R^3$ is alkylthio, halogenoalkoxy, halogenoalkylthio, alkenyl, alkoxycarbonyl or cyano, or in each case optionally substituted phenyl, phenoxy, phenylthio, phenylalkoxy or phenylalkylthio,
n is 0, 1 or 2,
m is 0 or 1, and
Het is optionally substituted dioxolanyl or dioxanyl,
or an addition product thereof with acids or metal salts, which exhibit fungicidal activity.

7 Claims, No Drawings

FUNGICIDAL HYDROXYALKYNYL-AZOLYL DERIVATIVES

The invention relates to new hydroxyalkynyl-azolyl derivatives, a process for their preparation and their use as fungicides.

It has already been disclosed that certain 3,3-dimethyl-1-(1,2,4-triazol-1-yl)-2-butanols, such as, for example, 2-(4-biphenylyloxymethyl)-3,3-dimethyl-1-(1,2,4-triazol-1-yl)-2-butanol and 2-(4-chlorophenylacetylenyl)-3,3-dimethyl-1-(1,2,4-triazol-1-yl)-2-butanol, have good fungicidal properties (compare DE-OS (German Published Specification) No. 3,018,866 and EP-OS (European Published Specification) No. 0,052,424). However, the action of these compounds is not always completely satisfactory, especially when low amounts and concentrations are applied.

New hydroxyalkynyl-azolyl derivatives of the general formula (I)

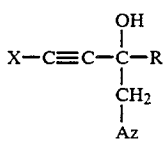

in which
Az represents 1,2,4-triazolyl or imidazolyl,
X represents optionally substituted phenyl or alkyl and
R represents the grouping

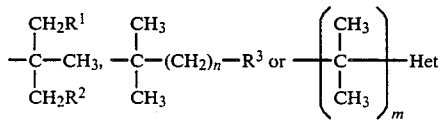

wherein
$R^1$ represents hydrogen or halogen,
$R^2$ represents halogen,
$R^3$ represents alkylthio, halogenoalkoxy, halogenoalkylthio, alkenyl, alkoxycarbonyl or cyano, or in each case optionally substituted phenyl, phenoxy, phenylthio, phenylalkoxy or phenylalkylthio,
n represents the number 0, 1 or 2,
m represents the number 0 or 1 and
Het represents optionally substituted dioxolanyl or dioxanyl,
and acid addition salts and metal salt complexes thereof, have been found.

The compounds of the formula (I) have an asymmetric carbon atom and can therefore be obtained in the two optical isomer forms.

It has furthermore been found that the new hydroxyalkynyl-azolyl derivatives of the general formula (I)

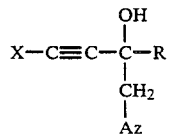

in which
Az represents 1,2,4-triazolyl or imidazolyl,
X represents optionally substituted phenyl or alkyl and
R represents the grouping

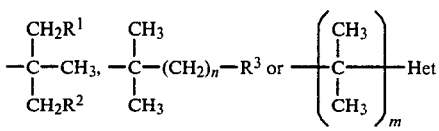

wherein
$R^1$ represents hydrogen or halogen,
$R^2$ represents halogen,
$R^3$ represents alkylthio, halogenoalkyl, halogenoalkylthio, alkenyl, alkoxycarbonyl or cyano, or in each case optionally substituted phenyl, phenoxy, phenylthio, phenylalkoxy or phenylalkylthio,
n represents the number 0, 1 or 2,
m represents the number 0 or 1 and
Het represents optionally substituted dioxolanyl or dioxanyl,
are obtained by a process in which azolyl ketones of the general formula (II)

in which
Az and R have the abovementioned meaning,
are reacted with acetylene derivatives of the general formula (III)

in which
X has the abovementioned meaning,
in the presence of a base and a diluent and, if appropriate, in the presence of a phase transfer catalyst.

If desired, an acid or a metal salt can then be added onto the compounds of the formula (I) thus obtained.

It has also been found that the hydroxyalkynyl-azolyl derivatives of the general formula (I) have powerful fungicidal properties.

Surprisingly, the hydroxyalkynyl-azolyl derivatives of the formula (I) according to the invention have better fungicidal actions than the abovementioned 3,3-dimethyl-1-(1,2,4-triazol-1-yl)-2-butanols which are known from the prior art and are closely related compounds structurally and from the point of view of their action. The active compounds according to the invention thus represent an enrichment of the art.

Formula (I) provides a general definition of the hydroxyalkynyl-azolyl derivatives according to the invention. Preferably, in this formula,
Az represents 1,2,4-triazol-1-yl or imidazol-1-yl;
X represents straight-chain or branched alkyl with 1 to 4 carbon atoms, or phenyl which is optionally mono-, di-, tri-, tetra- or penta-substituted by identical or different substituents, substituents which may be mentioned being: halogen, alkyl with 1 to 4 carbon atoms, alkoxy and alkylthio with in each case 1 or 2 carbon atoms, halogenoalkyl, halogenoalkoxy and halogenoalkylthio with in each case 1 or 2 carbon atoms and 1 to 5 identical or different halogen atoms, such as fluorine and chlorine atoms, the aldoxime or ketoxime radical and ether derivatives thereof, and phenyl, phenoxy, benzyl and benzyloxy, in each case optionally substituted by halogen or alkyl with 1 or 2 carbon atoms; and R represents the grouping

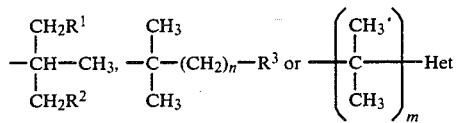

wherein
R¹ represents hydrogen, fluorine, chlorine or bromine,
R² represents fluorine, chlorine or bromine,
R³ represents alkylthio with 1 4 carbon atoms, halogenoalkoxy or halogenoalkylthio with in each case 1 or 2 carbon atoms and 1 to 5 identical or different halogen atoms, such as fluorine or chlorine atoms, alkenyl with 2 to 6 carbon atoms, alkoxycarbonyl with 1 to 4 carbon atoms in the alkyl part, cyano, or phenyl, phenoxy, phenylthio, phenylalkoxy with 1 to 4 carbon atoms in the alkyl part or phenylalkylthio with 1 to 4 carbon atoms in the alkyl part, in each case optionally mono-, di-, tri-, tetra- or penta-substituted by identical or different substituents, preferred substituents on the phenyl which may be mentioned in each case being: halogen, alkyl with 1 to 4 carbon atoms; alkoxy and alkylthio with in each case 1 or 2 carbon atoms; halogenoalkyl, halogenoalkoxy and halogenoalkylthio with in each case 1 or 2 carbon atoms and 1 to 5 identical or different halogen atoms, such as, in particular, fluorine and chlorine atoms, cyclohexyl, dialkylamino with 1 to 4 carbon atoms in each alkyl part, nitro, cyano, alkoxycarbonyl with 1 to 4 carbon atoms in the alkyl part and phenyl which is optionally substituted by halogen, n represents the number 0, 1 or 2, Het represents dioxolan-2-yl or 1,3-dioxanyl, in each case optionally mono-, di-, tri- or tetra-substituted by identical or different substituents, substituents which may be mentioned being: alkyl with 1 to 4 carbon atoms, and phenyl and phenoxyalkyl with 1 to 4 carbon atoms in the alkyl part, in each case optionally mono-, di-, tri-, tetra-or penta-substituted by identical or different substituents, substituents on the phenyl which may be mentioned being: halogen, alkyl with 1 to 4 carbon atoms, alkoxy and alkylthio with in each case 1 or 2 carbon atoms and halogenoalkyl, halogenoalkoxy and halogenoalkylthio with in each case 1 or 2 carbon atoms and 1 to 5 identical or different halogen atoms, such as, preferably, fluorine and chlorine atoms, and m represents the number 0 or 1.

Particularly preferred compounds of the formula (I) are those
Az represents 1,2,4-triazol-1-yl or imidazol-1-yl;
in which
X represents methyl, ethyl or tert.-butyl, or phenyl which is optionally mono-, di- or tri-substituted by identical or different substituents, substituents which may be mentioned being: fluorine, chlorine, bromine, methyl, tert.-butyl, methoxy, methylthio, trifluoromethyl, trifluoromethoxy, trifluoromethylthio, hydroximinomethyl, 1-hydroximinoethyl, methoximinomethyl and 1-methoximinoethyl, and phenyl, phenoxy, benzyl and benzyloxy, in each case optionally substituted by fluorine, chlorine and/or methyl; and R represents the grouping

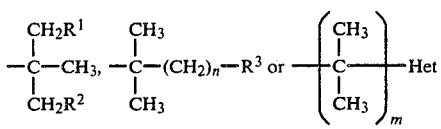

wherein
R¹ represents hydrogen, fluorine or chlorine;
R² represents fluorine or chlorine;
R³ represents methylthio, ethylthio, trifluoromethoxy, trifluoromethylthio, vinyl, methoxycarbonyl, ethoxycarbonyl or cyano, or phenyl, phenoxy, phenylthio, phenylmethoxy or phenylmethylthio, in each case optionally mono- or di-substituted by identical or different substituents, substituents on the phenyl which may be mentioned in each case being: fluorine, chlorine, methyl, ethyl, methoxy, methylthio, trifluoromethyl, trifluoromethoxy, trifluoromethylthio, dimethylamino, methoxycarbonyl and ethoxycarbonyl; n represents the number 0, 1 or 2;

Het represents dioxolan-2-yl, 1,3-dioxan-5-yl or 1,3-dioxan-2-yl, in each case optionally mono-, di- or tri-substituted by identical or different substituents, substituents which may be mentioned being: methyl, ethyl, n-propyl and isopropyl, and phenyl and phenoxymethyl, in each case optionally mono-, di- or tri-substituted by identical or different substituents from the group comprising fluorine, chlorine, methyl, trifluoromethyl and trifluoromethoxy, and m represents the number 0 or 1.

Further preferred compounds according to the invention are addition products of acids and those hydroxyalkynyl-azolyl derivatives of the formula (I) in which the substituents Az, R and X have the meanings which have already been given as preferred for these substituents.

Preferred acids which can be added on include hydrogen halide acids, such as, for example, hydrochloric acid and hydrobromic acid, especially hydrochloric acid, and furthermore phosphoric acid, nitric acid, mono-functional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acid, such as, for example, p-toluene-sulphonic acid and 1,5-naphthalenedisulphonic acid.

Other preferred compounds according to the invention are addition products of salts of metals of main groups II to IV and of sub-groups I and II and IV to VIII and those hydroxyalkynyl-azolyl derivatives of the formula (I) in which the substituents Az, R and X have the meanings which have already been mentioned as preferred for these substituents.

In this context, salts of copper, zinc, manganese, magnesium, tin, iron and nickel are particularly preferred. Possible anions of these salts are those which are derived from acids which lead to physiologically acceptable addition products. Particularly preferred acids in this connection are the hydrogen halide acids, such as, for example, hydrochloric acid and hydrobromic acid, and furthermore phosphoric acid, nitric acid and sulphuric acid.

If, for example, 3,3-dimethyl-4-fluoro-1-(1,2,4-triazol-1-yl)-2-butanone and 4-chlorophenyl-acetylene are used as starting substances, the course of the process according to the invention can be represented by the following equation:

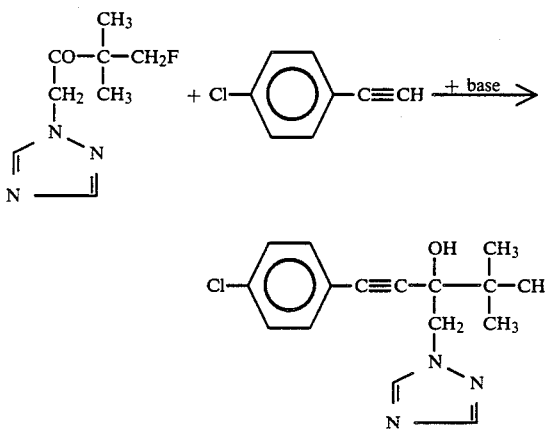

Formula (II) provides a general definition of the azolyl ketones to be used as starting substances in carrying out the process according to the invention.

The azolyl ketones of the general formula (II) are known (compare, for example, DE-OS (German Published Specification) No. 2,820,361 corresponding to U.S. Ser. No. 31,098, abandoned and EP-OS (European Published Specification) No. 0,043,923; they are the subject of German Patent Applications No. P 32 22 220 of 12.6.1982 corresponding to U.S. Ser. No. 498,605, filed 5/27/83 and No. P 32 24 129 of 29.6.1982, and they can be prepared by processes which are known in principle.

Formula (III) provides a general definition of the acetylene derivatives also to be used as starting substances for the process according to the invention.

The acetylene derivatives of the formula (III) are generally known compounds of organic chemistry.

Possible diluents for the process according to the invention are inert organic solvents.

These include, preferably, ethers, such as tetrahydrofuran, dioxane, ethylene glycol diethyl ether, diethylene glycol dimethyl ether and diethyl ether; aromatic hydrocarbons, such as benzene, chlorobenzene, o-dichlorobenzene and toluene; aliphatic hydrocarbons, such as hexane, cyclohexane and methylene chloride; acid amides, such as dimethylformamide and hexamethylphosphoric acid triamide; sulphoxides, such as dimethylsulphoxide; nitriles, such as acetonitrile; and acetals, such as butyraldehyde dibutyl acetal acetaldehyde dibutyl acetal and methylethyldioxolane.

The reaction according to the invention is carried out in the presence of a strong base. Preferred strong bases include alkali metal amides, hydrides and hydroxides, such as, for example, sodium amide, hydroxide or hydride and potassium amide, hydroxide or hydride; and also alkali metal alcoholates, such as potassium tert.-butylate; Grignard compounds, such as ethyl-magnesium bromide; and other organometallic compounds, such as butyl-lithium.

If appropriate, the reaction according to the invention is carried out in the presence of a phase transfer catalyst, such as, preferably, an ammonium or phosphonium compound, examples which may be mentioned being tetrabutylammonium bromide or chloride and triethylbenzylammonium chloride.

The reaction temperatures can be varied within a substantial range in carrying out the process according to the invention. In general, the reaction is carried out between $-80°$ and $+80°$ C., preferably at $-10°$ to $+40°$ C. If a phase transfer catalyst is used, the reaction is carried out between 40° and 150° C., preferably from 70° to 120° C.

Equimolar amounts of the starting materials are preferably used in carrying out the process according to the invention. The end products are isolated in the customary manner.

In a particular embodiment, the reaction according to the invention is carried out in a two-phase system, such as, for example, aqueous sodium or potassium hydroxide solution/toluene or methylene chloride, if necessary with the addition of 0.1-1 mol of a phase transfer catalyst.

Those acids which have already been mentioned as preferred acids in connection with the description of the acid addition salts according to the invention can preferably be used for the preparation of acid addition salts of the compounds of the general formula (I).

The acid addition salts of the compounds of the formula (I) can be obtained in a simple manner by customary salt formation methods, for example by dissolving a compound of the general formula (I) in a suitable inert solvent and adding the acid, for example hydrochloric acid, and they can be isolated in a known manner, for example by filtration, and if appropriate purified by washing with an inert organic solvent.

Those salts of metals which have already been described above are preferably used for the preparation of metal salt complexes of the compounds of the general formula (I).

The metal salt complexes of the compounds of the general formula (I) can be obtained in a simple manner by customary processes, thus, for example, by dissolving the metal salt in alcohol, for example ethanol, and adding the solution to compounds of the formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating cereal diseases, such as against powdery mildew on barley (*Erysiphe graminis*) or against brown rust on wheat (*Puccinia recondita*); for combating species of Uromyces, such as against the bean rust causative organism (*Uromyces appendiculatus*);

and for combating rice diseases, such as *Pyricularia oryzae* and *Pellicularia sasakii*.

The active compounds can be converted to the customary formulations, such as solutions, emulsions, wettable powders, suspensions, powders, dusts, foams, pastes, soluble powders, granules, aerosols, suspension-emulsion concentrates, seed treatment powder, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and-/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g are generally required.

For the treatment of soil, active compound concentrations of 0.00001 to 0.1% by weight, preferably 0.0001 to 0.02%, are required at the place of action.

PREPARATION EXAMPLES

Example 1

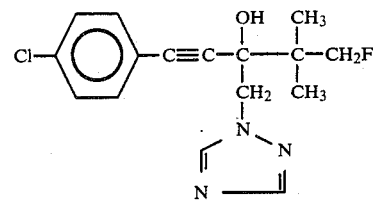

62 ml of butyl-lithium (15% strength in hexane, 0.1 mol) are added dropwise to 13.65 g (0.1 mol) of 4-chlorophenyl-acetylene in 50 ml of absolute tetrahydrofuran at 0° C., under nitrogen. The mixture is subsequently stirred at 0° C. for 15 minutes, and 18.5 g (0.1 mol) of 3,3-dimethyl-4-fluoro-1-(1,2,4-triazol-1-yl)-2-butanone in 30 ml of absolute tetrahydrofuran are then added dropwise. Thereafter, the reaction mixture is allowed to warm to room temperature and is subsequently stirred for 14 hours. It is concentrated by distilling off some of the solvent, the residue is taken up in ether and the mixture is washed neutral with water, dried over sodium sulphate and concentrated. The residue is recrystallized from diisopropyl ether. 19.9 g (61.9% of theory) of 1-(4-chlorophenyl)-4,4-dimethyl-5-fluoro-3-(1,2,4-triazol-1-ylmethyl)-1-pentin-3-ol or melting point 120° C. are obtained.

The following compounds of the general formula (I)

(I)

are obtained analogously and according to the process conditions described:

| Example No. | R | X | Az | Melting point (°C.) |
|---|---|---|---|---|
| 2 | —C(CH$_3$)$_2$—CH$_2$Cl | Cl—⟨C$_6$H$_4$⟩— | —N(N=CH—CH=N) | 129 |
| 3 | —C(CH$_2$F)$_2$—CH$_3$ | Cl—⟨C$_6$H$_4$⟩— | —N(N=CH—CH=N) | 128 |
| 4 | —C(CH$_3$)$_2$—(OCH$_2$CH$_2$O) | Cl—⟨C$_6$H$_4$⟩— | —N(N=CH—CH=N) | 143 |
| 5 | —C(CH$_3$)$_2$—(OCH$_2$CH$_2$O) | Cl—⟨C$_6$H$_4$⟩— | —N(N=CH—CH=N) | 86 |
| 6 | —C(CH$_3$)$_2$—(OCH(C$_2$H$_5$)CH$_2$O) | —Cl—⟨C$_6$H$_4$⟩— | —N(N=CH—CH=N) | 103 |
| 7 | —C(CH$_3$)$_2$—(OCH(C$_2$H$_5$)CH$_2$O) | Cl—⟨C$_6$H$_4$⟩— | —N(N=CH—CH=N) | 97 |
| 8 | —C(CH$_3$)$_2$—(OCH(C$_3$H$_7$)CH$_2$O) | Cl—⟨C$_6$H$_4$⟩— | —N(N=CH—CH=N) | 81–83 |
| 9 | —C(CH$_3$)$_2$—(OCH(C$_3$H$_7$)CH$_2$O) | Cl—⟨C$_6$H$_4$⟩— | —N(N=CH—CH=N) | 93 |
| 10 | —C(CH$_3$)$_2$—(OCH(CH$_3$)CH$_2$O) | Cl—⟨C$_6$H$_4$⟩— | —N(N=CH—CH=N) | 96 |
| 11 | —C(CH$_3$)$_2$—(OCH(CH$_3$)CH$_2$O) | Cl—⟨C$_6$H$_4$⟩— | —N(N=CH—CH=N) | 101 |
| 12 | —C(CH$_3$)$_2$—CH$_2$F | (CH$_3$)$_3$C— | —N(N=CH—CH=N) | 101 |

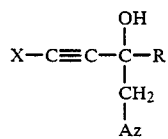

$$X-C\equiv C-\underset{\underset{Az}{\overset{|}{CH_2}}}{\overset{\overset{OH}{|}}{C}}-R$$

USE EXAMPLES

The known substances shown below are used as comparison compounds in the use examples which follow:

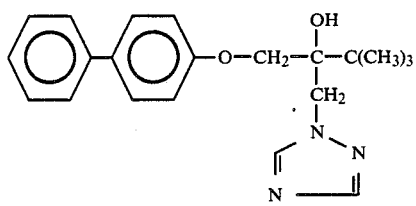
(A)

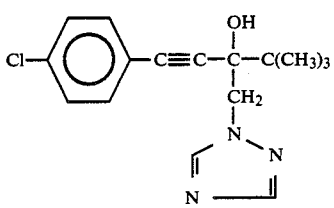
(B)

Example A

Erysiphe test (barley)/protective

Solvent: 100 parts by weight of dimethylformamide

Emulsifier: 0.25 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to the following preparation examples: 2, 1 and 3.

Example B

Puccinia test (wheat)/protective

Solvent: 100 parts by weight of dimethylformamide

Emulsifier: 0.25 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of Puccinia recondita in a 0.1% strength aqueous agar solution. After the spore suspension has dried on, the plants are sprayed with the preparation of active compound until dew-moist. The plants remain in an incubation cabinet at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, a clearly superior activity compared with the prior art is shown, for example, by the compounds according to the following preparation examples: 1 and 3.

Example C

Uromyces test (dwarf beans)/protective

Solvent: 4.7 parts by weight of acetone

Emulsifier: 0.3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous uredospore suspension of the bean rust causative organism (Uromyces appendiculatus and remain in a dark humidity chamber at 20° to 22° C. and 100% relative atmospheric humidity for 1 day.

The plants are then placed in a greenhouse at 20° to 22° C. and a relative atmospheric humidity of 70 to 80% under intensive illumination for 9 days.

Evaluation is carried out 10 days after the inoculation.

In this test, a clearly superior activity compared with the prior art is shown, for example, by the compounds according to the following preparation examples: 2, 1 and 3.

It will be understood that the specification and examples are illustrative but not limitative of the present invention and that other embodiments within the spirit and scope of the invention will suggest themselves to those skilled in the art.

What is claimed is:

1. A hydroxyalkynyl-azolyl derivative of the formula

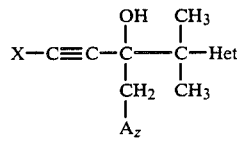

in which
- Az is 1,2,4-triazol-1-yl or imidazol-1-yl,
- X is phenyl which is optionally substituted by substituents independently selected from halogen, alkyl with 1 to 4 carbon atoms, alkoxy and alkylthio with in each case 1 or 2 carbon atoms, halogenoalkyl, halogenoalkoxy and halogenoalkylthio with in each case 1 to 2 carbon atoms and 1 to 5 identical or different halogen atoms, hydroximinomethyl, 1-hydroximinoethyl, methoximinomethyl, 1-methoximinoethyl, and phenyl, phenoxy, benzyl and benzyloxy in each case optionally substituted by halogen or alkyl with 1 or 2 carbon atoms,
- Het is dioxolan-2-yl or 1,3-dioxanyl in each case optionally substituted by substituents independently selected from alkyl with 1 to 4 carbon atoms, and phenyl and phenoxyalkyl with 1 to 4 carbon atoms in the alkyl part in each case optionally substituted on the phenyl by substituents independently selected from halogen, alkyl with 1 to 4 carbon atoms, alkoxy and alkylthio with in each case 1 or 2 carbon atoms, and halogenoalkyl, halogenoalkoxy and halogenoalkylthio with in each case 1 to 2 carbon atoms and 1 to 5 identical or different halogen atoms, or an addition product thereof with an acid or metal salt.

2. A compound or addition product according to claim 1, in which

X is phenyl which is optionally mono, di- or trisubstituted by substituents independently selected from fluorine, chlorine, bromine, methyl, tert.-butyl, methoxy, methylthio, trifluoromethyl, trifluoromethoxy, trifluoromethylthio, hydroximinomethyl, 1-hydroximinoethyl, methoximinomethyl, 1-methoximinoethyl, and phenyl, phenoxy, benzyl and benzyloxy in each case optionally substituted by fluorine, chlorine and methyl, and Het is dioxolan-2-yl, 1,3-dioxan-2-yl or 1,3-dioxan-5-yl in each case optionally mono-, di- or tri-substituted by substituents independently selected from methyl, ethyl, n-propyl, isopropyl, and phenyl and phenoxymethyl in each case optionally mono-, di- or tri-substituted by substituents independently selected from fluorine, chlorine, methyl, trifluoromethyl and trifluoromethoxy.

3. A compound according to claim 1, wherein such compound is 1-(4-chlorophenyl)-4-methyl-4-(1,3-dioxolane-2-yl)-3-(1,2,4-triazol-1-ylmethyl)-1-pentin-3-ol of the formula

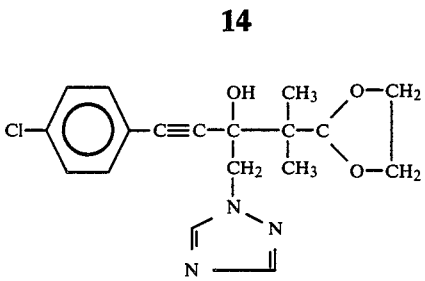

or an addition product thereof with an acid or metal salt.

4. A compound according to claim 1, wherein such compound is 1-(4-chlorophenyl)-4-methyl-4-(4-methyl-1,3-dioxolan-2-yl)-3-(1,2,4-triazol-1-ylmethyl)-1-pentin-3-ol of the formula

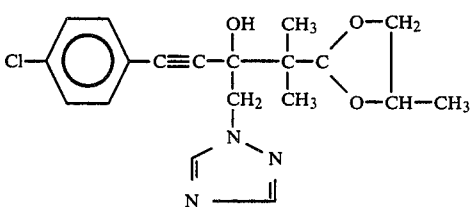

or an addition product thereof with an acid or metal salt.

5. A fungicidal composition comprising a fungicidally effective amount of a compound or addition product according to claim 1 plus a diluent.

6. A method of combating fungi which comprises administering to such fungi or to a fungus habitat a fungicidally effective amount of a compound or addition product according to claim 1.

7. The method according to claim 6 wherein such compound is
1-(4-chlorophenyl)-4-methyl-4-(1,3-dioxolan-2-yl)-3-(1,2,4-triazol-1-ylmethyl)-1-pentin-3-ol or
1-(4-chlorophenyl)-4-methyl-4-(4-methyl-1,3-dioxolan-2-yl)-3-(1,2,4-triazol-1-ylmethyl)-1-pentin-3-ol
or an addition product thereof with an acid or metal salt.

* * * * *